(12) United States Patent
Hussain et al.

(10) Patent No.: US 11,690,754 B2
(45) Date of Patent: Jul. 4, 2023

(54) SMART THERMAL PATCH FOR ADAPTIVE THERMOTHERAPY

(71) Applicant: KING ABDULLAH UNIVERSITY OF SCIENCE AND TECHNOLOGY, Thuwal (SA)

(72) Inventors: Muhammad Mustafa Hussain, Hercules, CA (US); Aftab Mustansir Hussain, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 386 days.

(21) Appl. No.: 16/912,101

(22) Filed: Jun. 25, 2020

(65) Prior Publication Data
US 2020/0323680 A1 Oct. 15, 2020

Related U.S. Application Data

(63) Continuation of application No. 15/307,247, filed as application No. PCT/IB2015/001409 on Apr. 20, 2015, now abandoned.
(Continued)

(51) Int. Cl.
*A61F 7/00* (2006.01)

(52) U.S. Cl.
CPC ...... *A61F 7/007* (2013.01); *A61F 2007/0071* (2013.01); *A61F 2007/0078* (2013.01);
(Continued)

(58) Field of Classification Search
CPC .............. A61F 7/007; A61F 2007/0071; A61F 2007/0077; A61F 2007/0078;
(Continued)

(56) References Cited

U.S. PATENT DOCUMENTS

2002/0094701 A1  7/2002  Biegelsen et al.
2004/0044384 A1  3/2004  Leber et al.
(Continued)

FOREIGN PATENT DOCUMENTS

DE   1012854 A1   10/1990
JP   3005930 U    1/1995
(Continued)

OTHER PUBLICATIONS

Office Action in corresponding/related Canadian Patent Application No. 2,946,814, dated May 4, 2021.
(Continued)

*Primary Examiner* — Kaitlyn E Smith
*Assistant Examiner* — Bradford C. Blaise
(74) *Attorney, Agent, or Firm* — Patent Portfolio Builders PLLC (57) ABSTRACT

A smart thermal patch for adaptive thermotherapy is provided. In an embodiment, the patch can be a stretchable, non-polymeric, conductive thin film flexible and non-invasive body integrated mobile thermal heater with wireless control capabilities that can be used to provide adaptive thermotherapy. The patch can be geometrically and spatially tunable on various pain locations. Adaptability allows the amount of heating to be tuned based on the temperature of the treated portion.

20 Claims, 11 Drawing Sheets

Related U.S. Application Data (60) Provisional application No. 61/984,918, filed on Apr. 28, 2014.

(52) U.S. Cl.
CPC ............... *A61F 2007/0093* (2013.01); *A61F 2007/0094* (2013.01); *A61F 2007/0098* (2013.01)

(58) Field of Classification Search
CPC ...... A61F 2007/0093; A61F 2007/0094; A61F 2007/0225; A61F 2007/0226; A61F 2007/0098
See application file for complete search history.

(56) References Cited

U.S. PATENT DOCUMENTS

| | | | |
|---|---|---|---|
| 2004/0175966 A1* | 9/2004 | Alger | H05K 7/1092 439/68 |
| 2004/0238819 A1 | 12/2004 | Maghribi et al. | |
| 2005/0082280 A1 | 4/2005 | Ferguson | |
| 2007/0135880 A1* | 6/2007 | Eggers | A61B 18/082 607/113 |
| 2007/0156208 A1 | 7/2007 | Havell et al. | |
| 2010/0116526 A1 | 5/2010 | Arora et al. | |
| 2011/0034912 A1 | 2/2011 | Graff et al. | |
| 2012/0035689 A1 | 2/2012 | Turtzo | |
| 2012/0245568 A1 | 9/2012 | Yu et al. | |
| 2013/0041434 A1 | 2/2013 | Youn et al. | |
| 2013/0333094 A1 | 12/2013 | Rogers et al. | |
| 2014/0207219 A1 | 7/2014 | Dunbar et al. | |
| 2015/0165231 A1 | 6/2015 | Scheja et al. | |
| 2015/0189753 A1* | 7/2015 | Goyal | H05K 1/148 29/830 |

FOREIGN PATENT DOCUMENTS

| | | |
|---|---|---|
| WO | 2006026459 A2 | 3/2006 |
| WO | 2009134823 A3 | 3/2010 |

OTHER PUBLICATIONS

Communication pursuant to Article 94(3) EPC in related European Application No. 15759934.1, dated Jul. 20, 2018 (References D1-4 provided in IDS filed Oct. 27, 2016).

Examination Report No. 1 in corresponding/related Australian Application No. 2015257402, dated Dec. 13, 2018 (Document D1 was previously cited in the IDS filed Oct. 27, 2016).

Examination Report No. 2 for Standard Patent Application in corresponding/related Australian Application No. 2015257402, dated Apr. 24, 2019 (Documents D1 and D2 were cited in the IDS filed Oct. 27, 2016 and Document D3 was cited in the Final Office Action dated Mar. 7, 2019).

Final Office Action in corresponding/related U.S. Appl. No. 15/307,247, dated Mar. 25, 2020.

Final Office Action in corresponding/related U.S. Appl. No. 15/307,247, dated Mar. 7, 2019.

GCC First Examination Report in related GC Application No. 2015-29304, dated Sep. 21, 2018 (Reference D1 provided with IDS filed Oct. 27, 2016).

Hsu; "Skin Patches Enable Smartphone-Controlled Pain Relief: A smart pain relief patch could prove a cheap, long-lasting solution for millions of arthritis sufferers" IEEE Spectrum, Published Online: Dec. 15, 2014; accessible at https//spectrum.ieee.org/tech-talk/biomedical/devices/skin-patches-enable-smartphoencontrolled-pain-relief.

International Search Report and Written Opinion of Application No. PCT/IB2015/001409 dated Oct. 16, 2015, 10 pages.

Kim et al., "Epidermal Electronics," Science, vol. 333, (www.sciencemag.org), Aug. 12, 2011, pp. 838-843, including"Supporting Online Material for Epidermal Electronics," Published Aug. 12, 2011, pp. 1-37. (Year: 2011).

Notice of Reasons for Rejection in corresponding/related Japanese Application No. 2016-565344, dated Nov. 27, 2018.

Notice of Reasons for Rejection in corresponding/related Japanese Patent Application No. 2016-565344, dated Jun. 25, 2019.

Office Action in corresponding/related U.S. Appl. No. 15/307,247, dated Jun. 26, 2019.

Office Action in corresponding/related U.S. Appl. No. 15/307,247, dated Oct. 10, 2019.

Office Action in corresponding/related U.S. Appl. No. 15/307,247, dated Sep. 27, 2018.

Second Written Opinion from the Intellectual Property Office of Singapore in corresponding/related SG Application No. 11201608961U, dated Jul. 16, 2019 (Documents D1-D4 were cited in an IDS filed Oct. 27, 2016, Documents D5-D8 were cited in an IDS filed Oct. 11, 2017, Document D9 was cited in an OA dated Sep. 27, 2018 and D10 was cited in an OA dated Mar. 7, 2019).

Written Opinion from the Intellectual Property Office of Singapore in related SG Application No. 11201608961U, dated Oct. 2, 2017.

\* cited by examiner

SMART THERMAL PATCH FOR ADAPTIVE THERMOTHERAPY

CROSS-REFERENCE TO RELATED APPLICATIONS

This application is a continuation of U.S. patent application Ser. No. 15/307,247, filed on Oct. 27, 2016, which is the National Stage of International Application No. PCT/IB2015/001409, filed 20 Apr. 2015, which claims the benefit of and priority to U.S. Provisional Application No. 61/984,918, filed on 28 Apr. 2014, having the title "SMART THERMAL PATCH FOR ADAPTIVE THERMOTHERAPY", the contents of all of which are incorporated by reference as if fully set forth herein.

BACKGROUND

In the United States, 50 million individuals, including 300,000 children, suffer from arthritis. As treatment, they commonly use thermotherapy. Commercially available chemical-based pain relief patches come in different sizes based on the pain locations, have limited heating ranges, are non-reusable and effective for limited hours with a shorter overall lifetime, are prone to side-effects (skin irritation, allergy), and are not suitable for children. Laser heating can also be used, however in the impoverished parts of the world both of these are expensive and mostly unavailable.

SUMMARY

Web integrated flexible and stretchable electronics for thermotherapy can offer affordable advanced healthcare, for example for Arthritis, pain-strain-sprain, cancer cell destruction and many more. We provide a smart thermal patch therefor. In an embodiment, the patch can be a stretchable, non-polymeric, conductive thin film flexible and non-invasive body integrated patch. It can include conductive material for thermal heating. It can be a skin contour integrated spatially tunable mobile thermal patch. It can include wireless controllability, adaptability (for example that tunes the amount of heat based on the temperature of the body location), reusability, and/or affordability due to low-cost complementary metal oxide semiconductor (CMOS) compatible integration. A lithographically patterned mechanical design can be included to absorb the deformation strain in the conductive thin film while retaining high conductivity. It can be stretched and contracted back to its original form, allowing its usage as a geometrically and spatially tunable thermal patch on various pain locations. Web and battery integration can be included to make it a completely autonomous-mobile low-cost (for example, $1-2) smart electronic system, with precise temperature control using smartphones or mobile gadgets.

In an embodiment a thermal patch is provided, comprising: an array of heating pads; and a plurality of stretchable conductors interconnecting each of the array of heating pads with adjacent heating pads. In any one or more aspects the array of heating pads can be interconnected between a plurality of contact pads. The plurality of contact pads can be connected to adjacent heating pads by stretchable conductors. The thermal patch can include or be connected to a battery. The thermal patch can include or be connected to a flexible microcontroller. The thermal patch can include or be connected to a wireless transceiver configured to communicate with a mobile computing device. The wireless transceiver can be a Bluetooth transceiver. The mobile computing device can be a smart phone.

In an embodiment, a method is provided, comprising: a) forming a mask on a polymer layer, the mask defining a thermal patch; b) etching the polymer layer; c) depositing a conductive material to form stretchable conductors of the thermal patch; and d) vapor phase etching to release the thermal patch. In any one or more aspects, the mask can be an aluminum mask. The polymer layer can be a polyimide (PI) layer. The conductive material can be a metal, preferably copper, nickel, chromium, tin, silver, platinum or a metal alloy. The method can include wet etching to remove the mask prior to depositing the conductive material. The method can include depositing a seed layer for depositing the conductive material. The vapor phase etching can be $XeF_2$ vapor phase etching. In any one or more of the various embodiments the stretchable conductor(s) can have a lateral spring design. The design of the conductors can make them behave hyperelastically allowing the conductor(s) to stretch under applied strain and return to their generally unstretched shape when the strain is released.

Other systems, methods, features, and advantages of the present disclosure will be, or will become, apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Disclosed herein are various examples related to a smart thermal patch for adaptive thermotherapy. Reference will now be made in detail to the description of the embodiments as illustrated in the drawings, wherein like reference numbers indicate like parts throughout the several views.

As an effective alternative to chemical-based pain relief patches and laser heating, a wirelessly controllable heater can be used for the application of heat on specific points on the skin or thermotherapy. The use of thermotherapy has been proven useful for treating various serious diseases like arthritis, cancer, etc. The use of thin film-based thermal heaters on the human body has been restricted due to their natural rigidity and limited stretchability. Most material systems in use in electronics are not inherently stretchable. In particular, copper lines are commonly used as interconnects in state-of-the-art electronics. Since copper has a yield strain of 20-25%, the use of copper interconnects in stretchable electronics is restricted. Compatibility with large deformations can be provided by web integrated flexible and stretchable electronic devices that retain their electrical and thermal properties upon application of large strains (>100%).

In an embodiment, the patch can be a stretchable, non-polymeric, conductive thin film flexible and non-invasive body integrated mobile thermal heater with wireless control capabilities that can be used to provide adaptive thermotherapy. The patch can be geometrically and spatially tunable on various pain locations. Adaptability allows the amount of heating to be tuned based on the temperature of the treated portion.

In one or more aspects, the conductive thin film can be a metallic thin film. As an example, low-cost complementary metal oxide semiconductor (CMOS) compatible integration can facilitate reusability and affordability of the device. Compared to prior demonstrations on stretchable electronics using mostly polymer or composite-based material systems involving 1D nanowires or 2D graphene for stretchable interconnects, electrodes, integrated circuits, light emitting diodes, super capacitors, artificial skins, and others, the smart thermal design enables the thin film's continued usage as a tunable-sized thermal heater by using design features to absorb the deformation strain in thin films with no impact on their low resistance. In an aspect the metallic thin film can be a copper (Cu) based thin film.

Based on the pain location and spatial requirements, the spatially tunable mobile thermal heater can be stretched to satisfy the user's needs and contracted back to its original form. The metallic nature of the film allows it to be used over a longer lifetime and in a reusable manner. Additionally, integration of web technology (such as advanced Bluetooth technology) and a battery can make it an autonomous mobile smart electronic system, with precise temperature control using a smartphone or other mobile interface device. The lithographically patterned mechanical design absorbs the deformation strain in the Cu (or other types of metallic) and conductive thin films while retaining their high conductivity, allowing the device to be stretched and contracted back to its original form. The geometrically and spatially tunable thermal patch can non-invasively conform to the skin contour at various pain locations. The availability of flexible and smart thermo-electronic systems with stretching capabilities enables their daily usage for thermotherapy by the global population, including patients, who are suffering from arthritis or more sophisticated cancerous tumor cell destruction, and individuals such as athletes or soldiers, who are experiencing body and/or muscle pains, strains, and sprains. As an example, the device can be used for thermotherapy (hyperthermia) for cancerous cell destruction. Moreover, we can use dissolvable conducting materials (examples include: tungsten, aluminum, molybdenum, etc.). After the treatment, the device can then be completely dissolved inside the body to eliminate any further surgery requirement to retract the device.

In one or more aspects, copper can be used as the conducting element since copper is used in state-of-the-art CMOS technology for metal interconnects, and is thus CMOS process compatible. Since copper is inherently non-stretchable, stretchability has been introduced by using a lateral spring design. In some implementations, other conductive materials, including conductive metals (e.g., nickel, chromium, tin, silver, platinum, or other metals or alloys) can also be used to form the metal interconnects.

Figure 1:
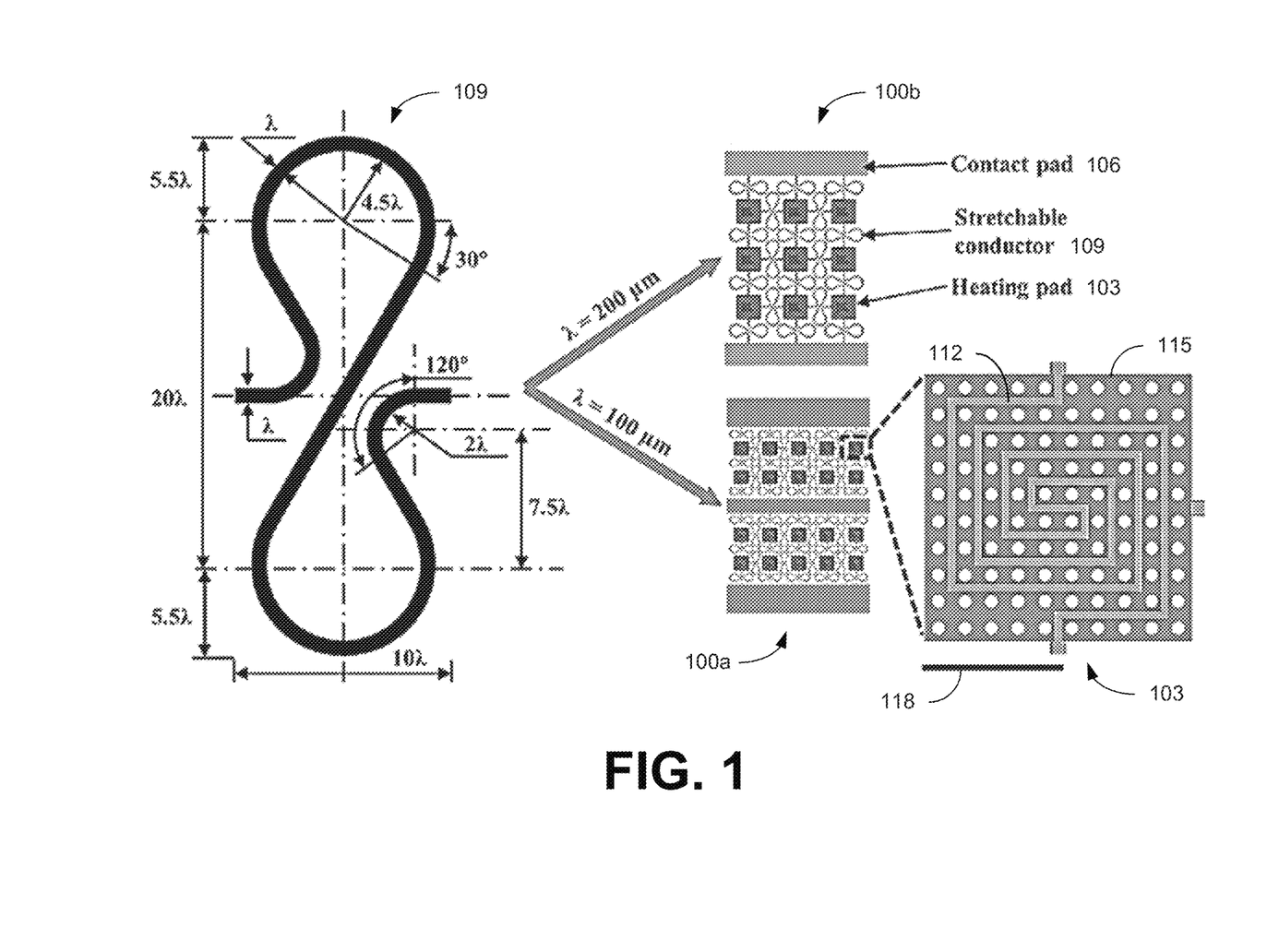
FIG. 1 is a graphical representation illustrating examples of thermal patches in accordance with various embodiments of the present disclosure.

Referring to FIG. 1, shown is an example of a thermal patch design 100. The design can be scaled using the scaling parameter $\lambda$ to obtain devices of different dimensions. To demonstrate the scalability of the design, two versions of the design were fabricated by scaling the design parameter $\lambda$ to 100 μm and 200 μm. As illustrated in FIG. 1, thermal patch devices 100a and 100b were fabricated and characterized with $\lambda$=100 μm and $\lambda$=200 μm, respectively. The thermal patch devices 100 can include one or more arrays or matrices of heating pads 103 interconnected between a plurality of contact pads 106 using stretchable conductors 109.

The conductors 109 can be formed having a spring design, for example a lateral spring design. They can be coiled in a dimension that allows for stretching or flexing of the conductors. A non-limiting example is depicted in FIG. 1 wherein the conductor 109 is coiled, having a generally figure "8" configuration to provide a lateral spring design. One skilled in the art will recognize that other shapes can be used to provide a lateral spring design. For example the conductor 109 can be coiled as shown in either the upper or lower portion depicted in FIG. 1 in a generally circular or oval shape. A coiled design can allow the conductor(s) 109 to behave as a spring. The spring or coiled design can make the conductor(s) 109 behave hyperelastically, as described in more detail below.

The heating pads 103 can be squares of size 202. Copper lines 112 (or other types of metallic lines) on the heating pads 103 are placed so as to maximize the length of the conductor, and hence the resistance, of the conductor. A polyimide (PI) pad 115 has holes of 100 μm diameter, separated by 200 μm (center-to-center). Other soft polymers with characteristics similar to PI can also be used for pad 115. The scale bar 118 is 1 mm. The contact pads 106 are 2 mm×20 mm in both cases. The total length ($L_t$) of the curved spring structure of the stretchable conductors 109 is 78.35$\lambda$, while the lateral length ($L_l$) of the spring is only 102. When the spring is stretched to its maximum capacity, the lateral length of the spring is approximately equal its total length. Hence, the stretchable lateral spring provides a maximum uniaxial stretchability of about 800% ($L_t/L_f$=7.835) for the individual stretchable conductors 109. As shown in FIG. 1, the stretchable conductors 109 are used to provide flexibility between heating pads 103 in two directions.

To demonstrate an application of the stretchable copper conductors 109, stretchable thermal patches 100 are configured with stretchable conductors 109 connecting adjacent heating pads 103 to provide flexibility in two directions. The heating pads 103 do not contribute to the stretching, and have a constant lateral length of 202, along with interconnects of length 52. This 52 length on both sides of the spring increases the lateral length before and after stretching, hence the stretchability at the device level is given by:

$$\frac{L_t}{L_i} = \frac{\left(78.35 + 2*\left(\frac{20}{2}\right) + 5 + 5\right)\lambda}{\left(2*\left(\frac{20}{2}\right) + 5 + 5 + 10\right)\lambda} = 2.71$$

Thus, with the heating pads included, the total stretchability of the thermal patch system becomes about 270%.

Figure 2:
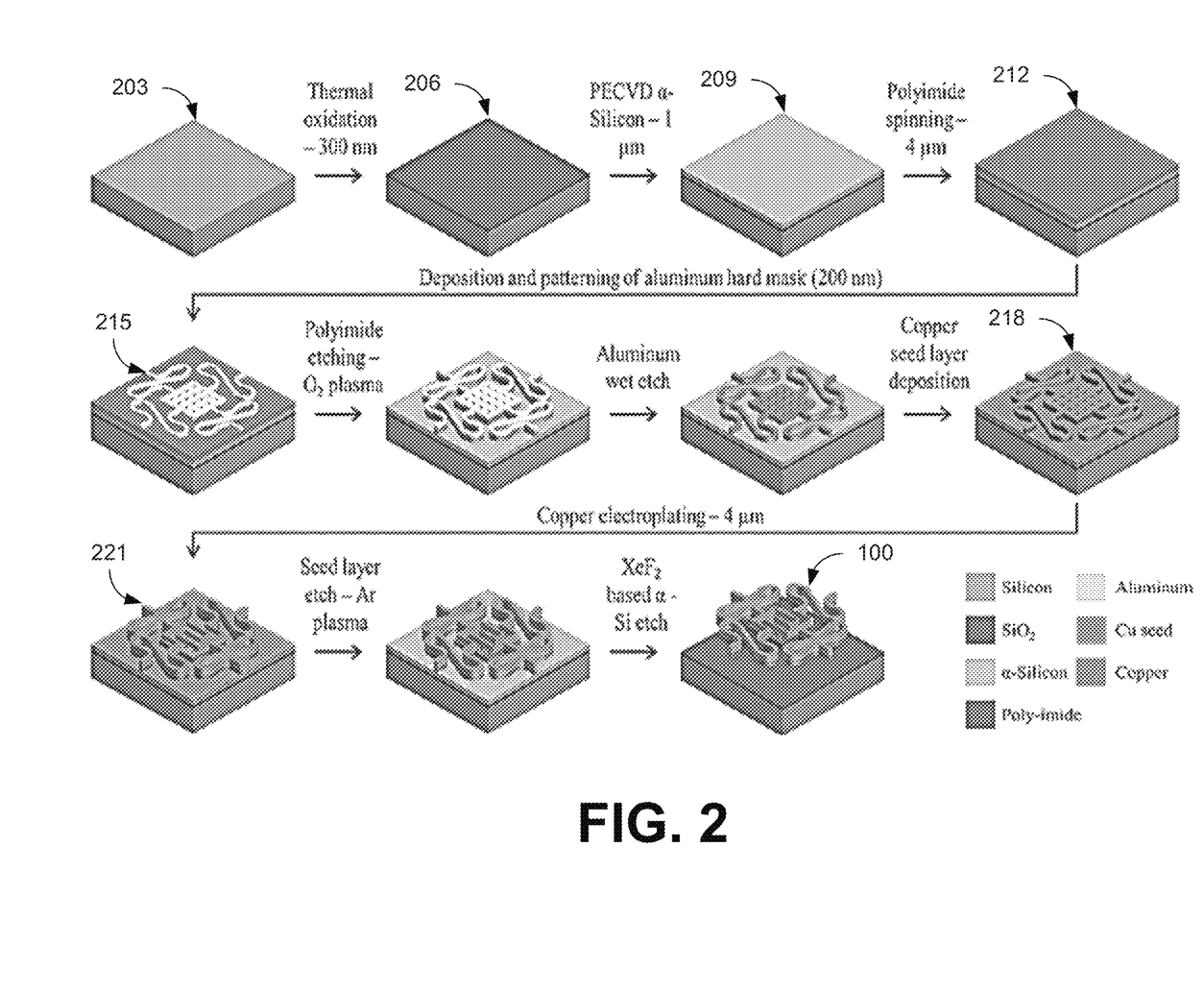
FIG. 2 is a graphical representation illustrating an example of fabrication on a thermal patch of FIG. 1 in accordance with various embodiments of the present disclosure.

Referring next to FIG. 2, shown is an example of a CMOS compatible process to directly fabricate the thermal patch 100 using metal (e.g., copper) lines 112 on a flexible (e.g., a polymer such as polyimide) surface making it a transferless process. Beginning with a silicon (Si) wafer 203, thermal oxidation is used form a silicon dioxide ($SiO_2$) layer 206. Plasma-enhanced chemical vapor deposition (PECVD) is then used to form a thin amorphous silicon ($\alpha$-silicon) sacrificial layer 209. A 4 μm thick polyimide (PI) layer 212 can then be spin-coated on the thermally oxidized wafer with the 1 μm thick amorphous silicon sacrificial layer 209. In some implementations, other polymers having characteristics similar to PI can be used to form the layer 212. The PI 212 is patterned into the lateral spring design using deposition and patterning of an aluminum hard mask 215 and $O_2$ plasma etching. Wet etching can be used to remove the aluminum mask 215. A seed layer 218 for copper electroplating is deposited on the PI 212, and 4 μm thick copper lines 221 are subsequently electroplated. The seed layer 218 is etched away using argon plasma and the thermal patch devices 100 are released using, e.g., $XeF_2$ based vapor phase etching of the amorphous silicon sacrificial layer 209. The thicknesses of the copper lines 221 and the PI layer 212 can be engineered to be the same, so that the neutral axis during bending is at the copper/PI interface. The PI pad 115 includes holes of 100 μm diameter, separated by 200 μm (center-to-center), to reduce the time required for $XeF_2$ gas phase release. Hence, the interface of the two materials is under no stress even during flexing.

Figure 3:
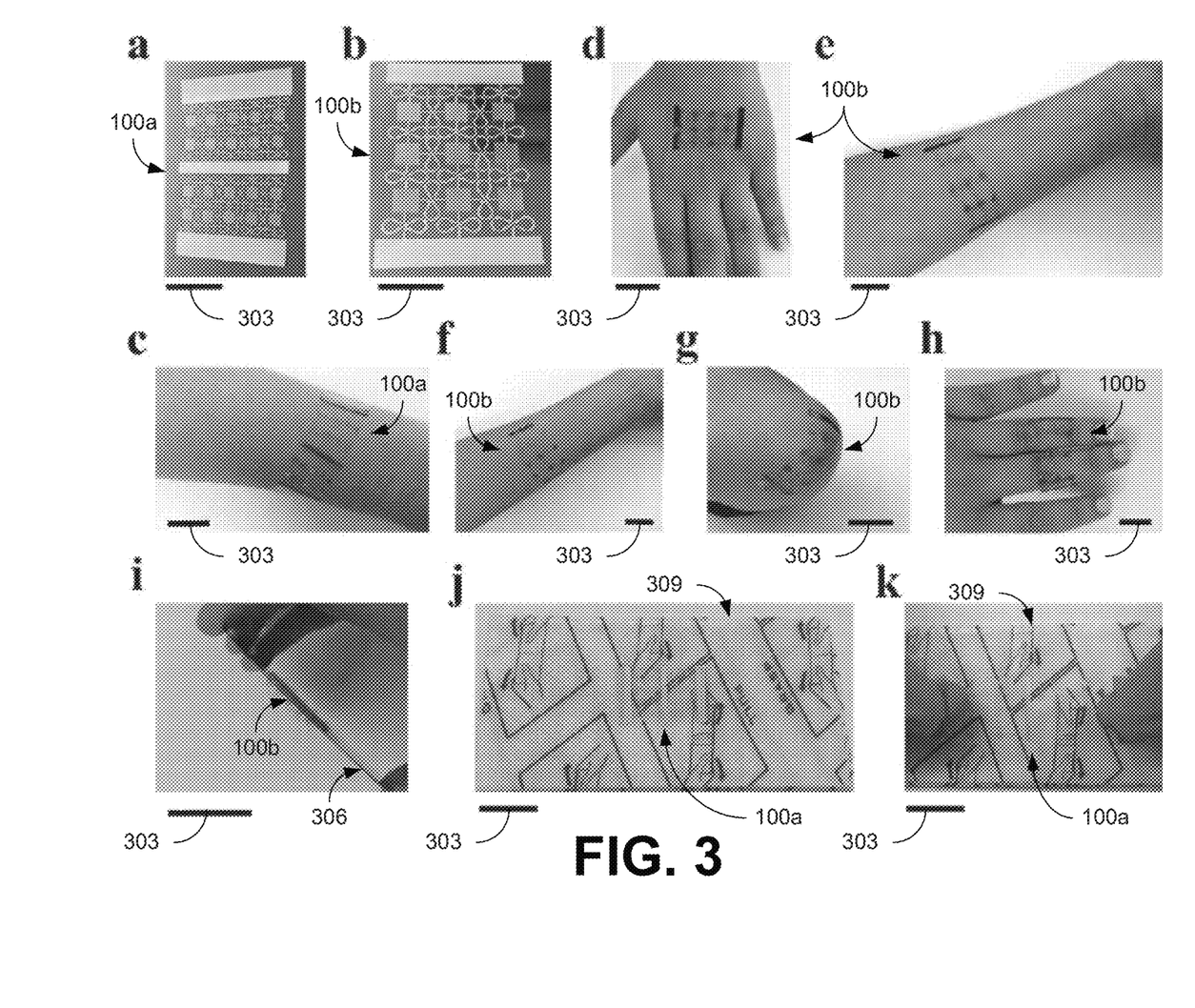
FIG. 3 includes images of examples of thermal patches of FIG. 1 in accordance with various embodiments of the present disclosure.

To fabricate working thermal patch devices 100 shown in FIG. 3, the starting point was a thermally oxidized (300 nm), 4" silicon (100) substrate 203. A 1 μm thick layer of amorphous silicon was deposited on the substrate 203 using PECVD (e.g., $SiH_4$, Ar plasma at 250° C. for 25 minutes) as a sacrificial layer 209. The wafer was then spun with polyimide (e.g., HD MircoSystems PI2611) at 4000 rpm for 60 seconds to obtain a 4 μm thick coating 212. The polyimide (PI) layer 212 was cured subsequently at 90° C. for 90 seconds, at 150° C. for 90 seconds, and at 350° C. for 30 minutes. A 200 nm aluminum layer was sputtered (25 sccm Ar plasma at 10 mTorr, 500 W DC power) on the wafer to act as hard mask 215 for the PI etching. The aluminum thin film was patterned using contact lithography and etched using Gravure Aluminum wet etchant (Technic France). The PI layer 212 was then etched using $O_2$ plasma at 60° C. and 800 mTorr, for 16 minutes. A Cr/Au (20/200 nm) bilayer was deposited on the wafer to act as a seed layer 218 for copper electroplating. A Cr/Cu bilayer can also be used as a seed layer 218 to reduce cost in batch fabrication. The wafer was spin-coated with photoresist, and the areas to be covered with copper were exposed by developing the photoresist. A 4 μm thick copper layer 221 was electroplated using $CuSO_4$ solution as the electrolyte and 0.698 Ampere current for 200 seconds. The photoresist was washed away using acetone and the seed layer 218 was etched using Ar (30 sccm) plasma for 3 minutes. The wafer was subjected to 60 cycles (30 seconds each) of $XeF_2$ etching (e.g., Xactix X3C) at 4 Torr pressure to release the thermal patch 100.

FIG. 3 includes images (a) through (k) of fabricated thermal patches 100. All scale bars 303 are 2 cm. Optical images of the thermal patches 100 after release are as shown in images (a) and (b) of FIG. 3 for A=100 μm and A=200 μm, respectively. The thermal patch 100a shown in image (a) includes two arrays of heating pads 103 between three contact pads 106. The application of the thermal patch 100a of image (a) on human skin, with 200% lateral strain, is shown in image (c). The application of the thermal patch 100b of image (b) on human skin in various locations is shown in images (d) through (h) of FIG. 3. In case of image (d), the thermal patch 100b is under no strain, while in image (e) the thermal patch 100b is under 150% uniaxial strain. Image (f) of FIG. 3 shows the thermal patch 100b under biaxial strain, with both lateral and transverse strain being 150%.

The flexibility of the fabricated thermal patch 100b when wrapped around various bodily features is illustrated in images (g) through (i) of FIG. 3, with a bending radius as low as 0.5 mm. Image (g) shows the thermal patch 100b conformally bent around an elbow joint with a bending radius of 6.3 cm. Image (h) shows the thermal patch 100b wrapped around two fingers with a bending radius 0.96 cm. Image (i) shows the thermal patch 100b wrapped around a silicon wafer 306 with a bending radius about 0.5 mm. The van der Waals force enables conformal placement on skin micro-irregularities. Images (j) and (k) of FIG. 3 compare an off-the-shelf medical patch 309 (WellPatch™ Capsaicin Pain Relief Patch) to the thermal patch 100a of image (a). In image (k), the thermal patch 100a is shown with a 200% strain.

Figure 4A:
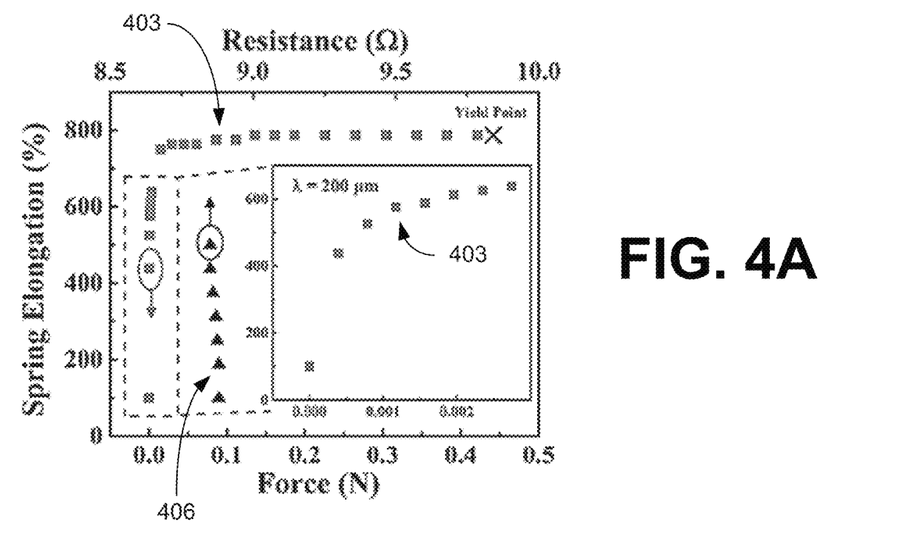
FIGS. 4A and 5A are examples of plots of spring elongation versus applied force of thermal patches of FIG. 1 in accordance with various embodiments of the present disclosure.
Figure 4B:
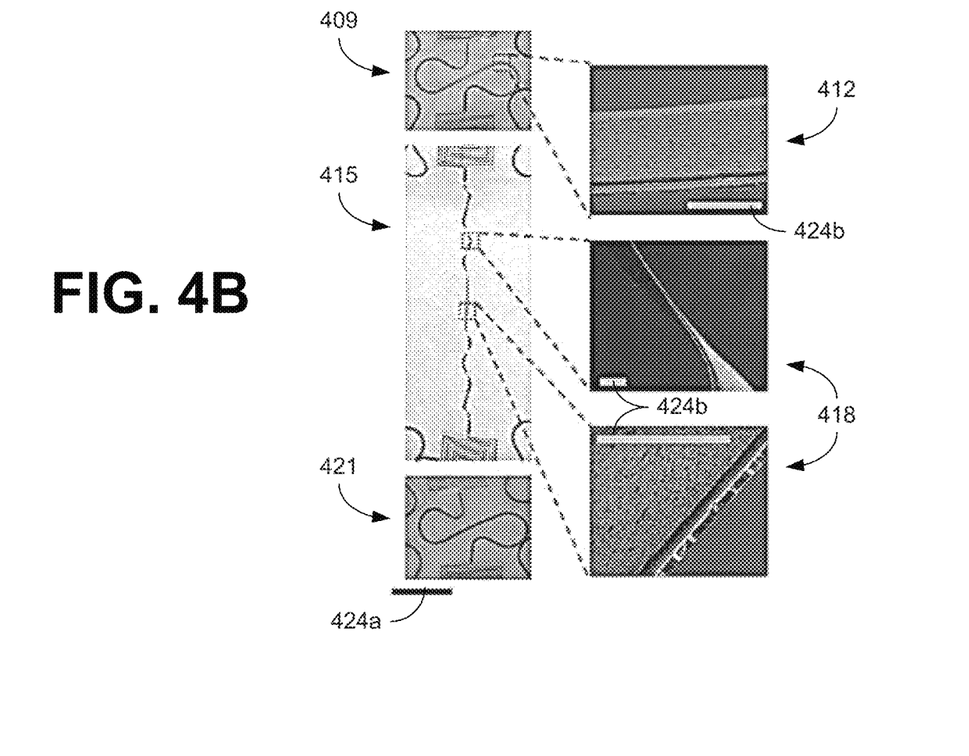
FIGS. 4B and 5B include images of spring elongation of FIGS. 4A and 5A in accordance with various embodiments of the present disclosure.
Figure 5A:
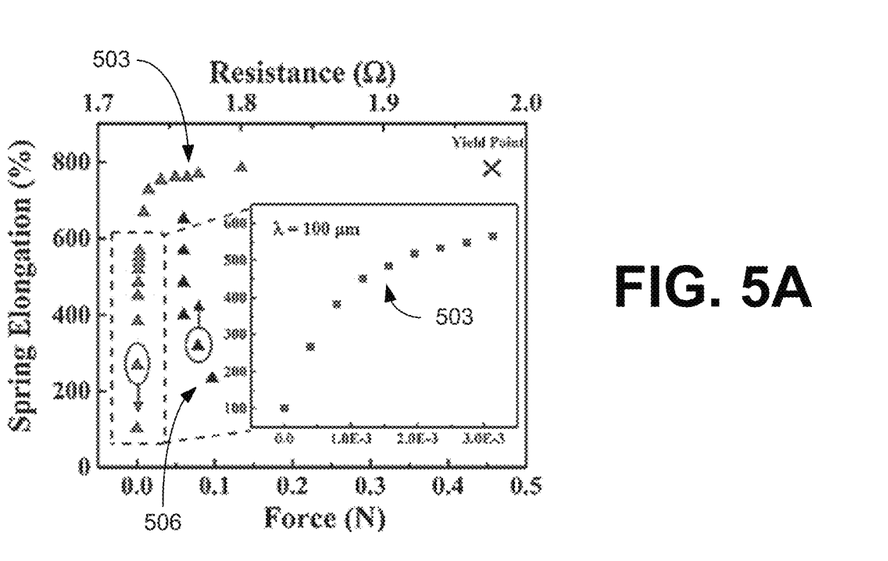

The mechanical performance of the stretchable conductors 109 under uniaxial tensile strain is summarized in FIGS. 4A-4B and 5A-5B for A=200 μm and A=100 μm, respectively. As previously discussed, a maximum stretchability of approximately 800% is possible for the individual springs. This translates into an overall maximum stretchability of the device of approximately 300%. However, it was observed that this maximum point was not reversible. Rather, the elastic limit for the springs was determined to be about 600%. FIGS. 4A and 5A are examples of plots of spring elongation versus applied force in the lateral direction (data set 403 for $\lambda$=200 μm and data set 503 for $\lambda$=100 μm), and resistance as a function of elongation for the first cycle (data set 406 for $\lambda$=200 μm and data set 506 for $\lambda$=100 μm), for a stretchable conductor 109. The force versus elongation plots 403 and 503 obtained for the springs closely resembles hyperelastic, rubber-like materials. The yield point is marked with an "x". The inset plots are the spring elongation versus applied force within the elastic limit. The stretchable conductors 109 returned back to their original state after 10 cycles of stretching up to 600%. Thus, the lateral spring design makes copper thin films behave hyperelastically.

For the stretchable conductors 109, the resistance data sets 406 and 506 of the thermal patches 100 were almost invariant with strain—variation of only 0.6% within the elastic limit. The consistency in the resistance of the springs with the applied strain may be attributed to the design of the lateral spring system. The applied strain was absorbed in the deformation of the spring design, hence the copper interconnect was, at no point, under strain. Hence, the resistance of the metal lines (and the complete thermal patch 100) remained unchanged throughout the experiment. Further, the slight variation in resistance shown in FIGS. 4A and 5A was only for the first stretching cycle. The resistance became constant after the first cycle of elongation and remained constant after several cycles of stretching. In particular, after 10 cycles, there was no change in the resistance of the springs with strain. This may be attributed to, with the first few cycles, the springs undergoing a slight reorientation of their metal grains to accommodate for the twisting in the lateral spring. Once the metal grains "settle", the resistance of the springs and the thermal patch 100 becomes invariant with respect to strain.

Figure 5B:
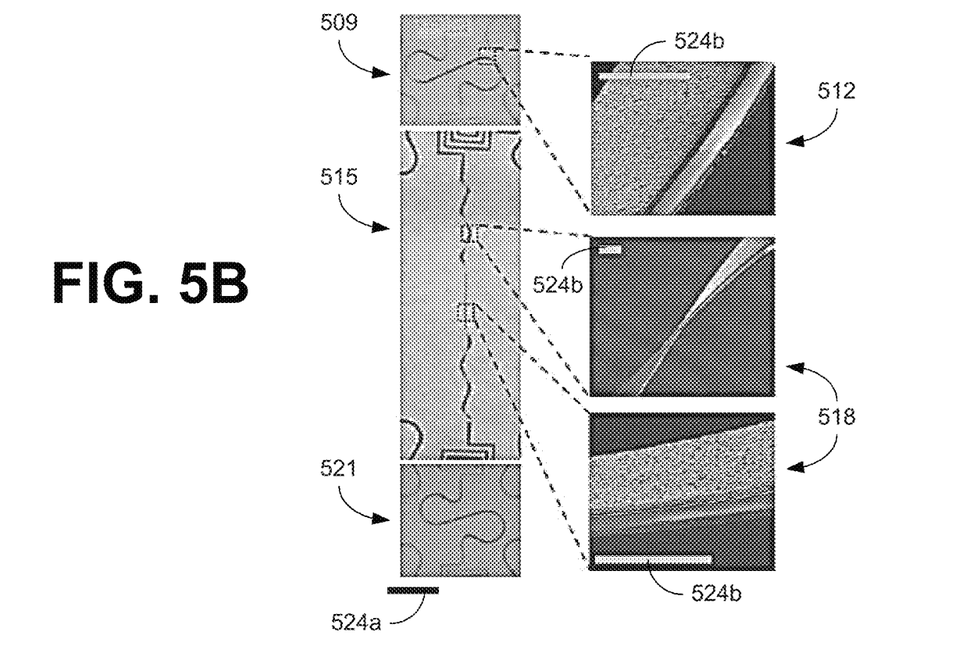

FIGS. 4B and 5B show images of stretchable conductors 109 with $\lambda$=200 μm and $\lambda$=100 μm, respectively, during elongation. The top images 409 and 509 show the spring before the beginning of elongation cycles. Images 412 and 512 are scanning electron micrographs (SEM) for the released spring. The middle images 415 and 515 show the spring completely stretched with about 800% spring elongation. Images 418 and 518 are SEMs of portions for the springs under tension with a strain of 200%. It can be seen that the lateral spring twists at certain points to absorb the strain energy. The bottom images 421 and 521 show the spring after 10 elongations cycles of 600% elongation within the elastic limit of the spring. For FIG. 4B, scale bar 424a is 2 cm and scale bars 424b are 50 μm. For FIG. 5B, scale bar 524a is 4 mm and scale bars 524b are 50 μm.

Heating capability and effective operational time can be limited for commercially available thermotherapy. FIGS. 6A-6C and 7A-7C illustrate the thermal performance assessment of the thermal patch 100 designs for $\lambda$=100 μm and $\lambda$=200 μm, respectively. As shown in FIG. 1, the heating pads 103 of the thermal patches 100 were contacted by soldering copper wires of the stretchable conductors 109 to the 2 mm×20 mm contact pads 106. The total parasitic resistance introduced into the thermal patch device 100 due to the contact pads 106 was measured to be 0.05 Ohm (or about 0.6% of the total device resistance). During the evaluation, the thermal patch 100 was energized using a constant voltage source (e.g., an Agilent E3631A power supply) and the temperature of the thermal patch device 100 was measured using an Optotherm Mirco thermal imaging system. To measure the average temperature of the glass substrate for a given applied voltage, a square area was defined with an area equal to four times the size of the heating pad 103 as a unit. The mean temperature of this unit area was plotted against voltage to obtain the thermal characteristics of the heating pad under thermal load (glass substrate).

Figure 6A:
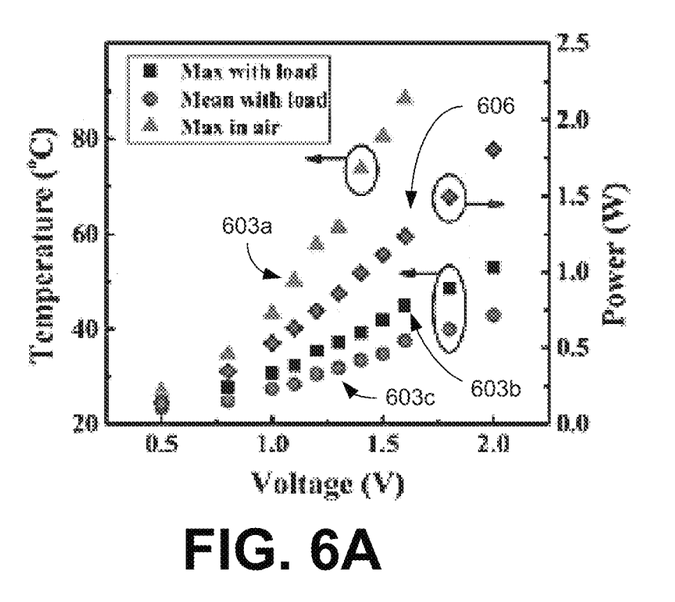
FIGS. 6A-6B and 7A-7B are examples of plots of temperature and power versus applied voltage of thermal patches of FIG. 1 in accordance with various embodiments of the present disclosure.
Figure 7A:
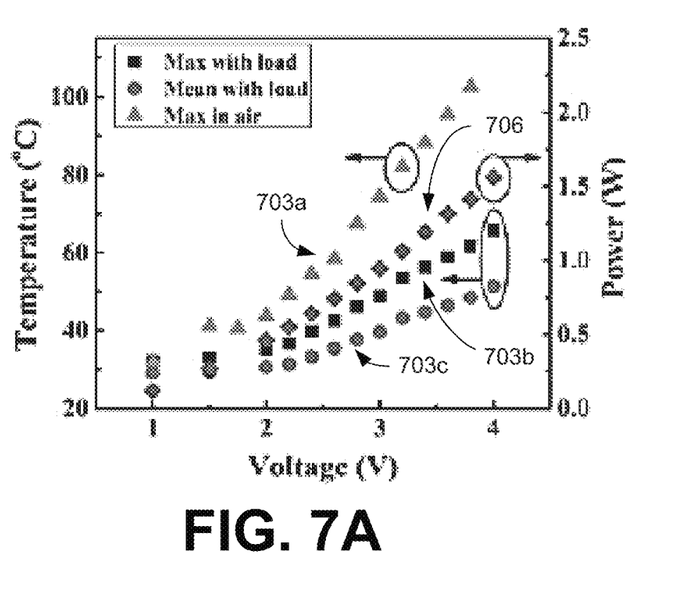

FIGS. 6A and 7A show examples of the temperature of the thermal patch 100 versus applied voltage (data sets 603 for $\lambda$=100 μm and data sets 703 for $\lambda$=200 μm) and the power consumed for the applied voltage (data set 606 for $\lambda$=100 μm and data set 706 for $\lambda$=200 μm). The maximum temperature for the thermal patch in air and on a glass substrate (with load) was plotted (data sets 603a/603b and 703a/703b, respectively) for an applied voltage. Image (i) of FIG. 3 shows a thermal patch 100b (FIG. 1) wrapped around a silicon wafer 306. The mean temperature data 603c and 703c corresponds to the mean of the temperature readings of the unit area defined as a square four times the heating pad 103 area.

As can be seen in FIGS. 6A and 7A, the thermal patches 100 achieved higher temperatures while in ambient air, as compared to the glass substrate load, for the same applied voltage. This is expected as air offers only convective cooling of the heating pad 103 (FIG. 1), while glass substrate offers convection through air (top portion) as well as conduction through the glass substrate, and has a higher thermal capacity. In the case of FIG. 6 ($\lambda$=100 μm), a maximum temperature of about 80° C. was measured for an applied voltage of 1.6 V with power consumption of 1.5 W. The temperature range with the glass substrate as thermal load is obtained as 25-53° C. In the case of FIG. 7 ($\lambda$=200 μm), a maximum temperature of 102° C. is recorded for 3.8 V applied voltage with a 1.4 W power consumption. The temperature range in case with glass substrate as thermal load is obtained as 25-66° C.

Figure 6B:
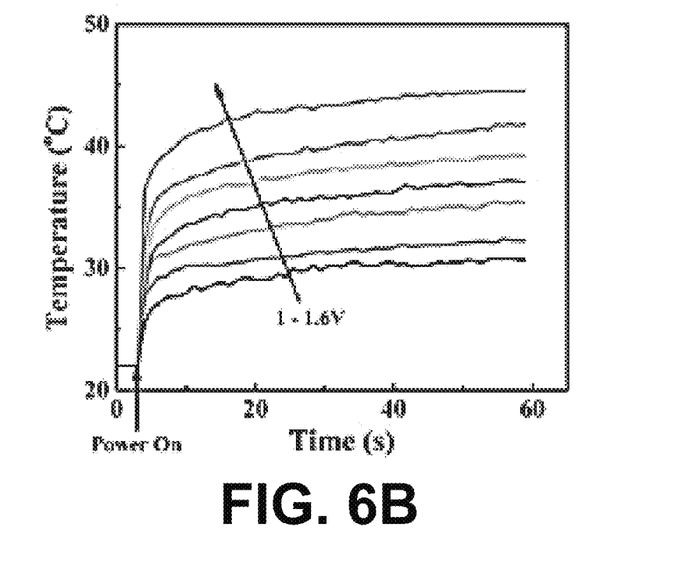
Figure 6C:
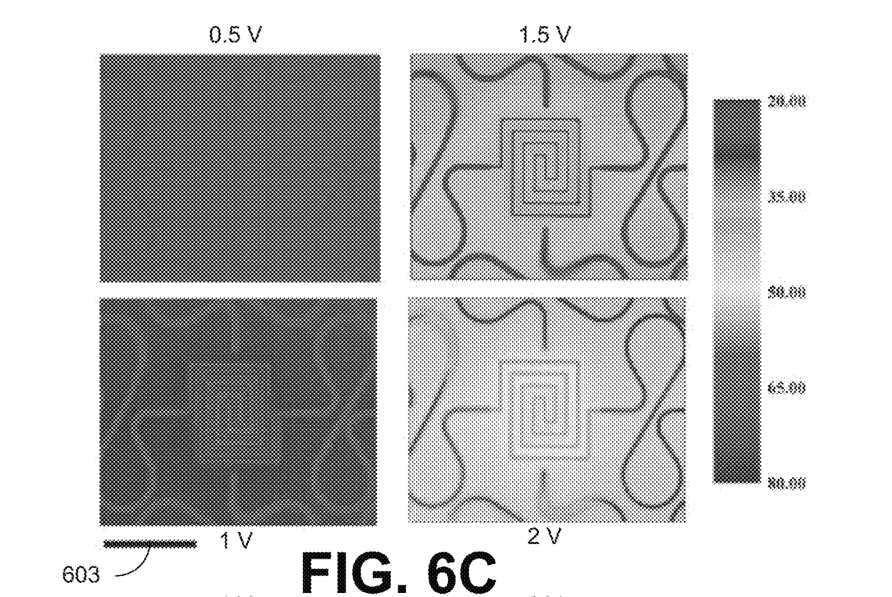
FIGS. 6C and 7C are examples of plots of temperature of the thermal patches of FIG. 1 for various applied voltages in accordance with various embodiments of the present disclosure.
Figure 7B:
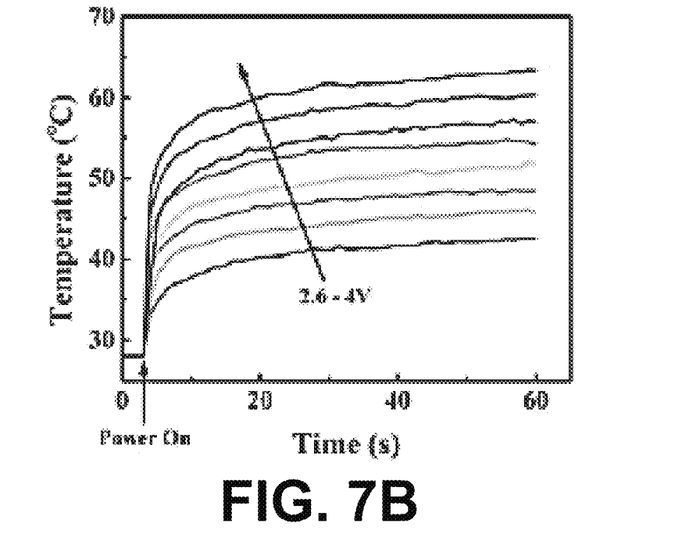
Figure 7C:
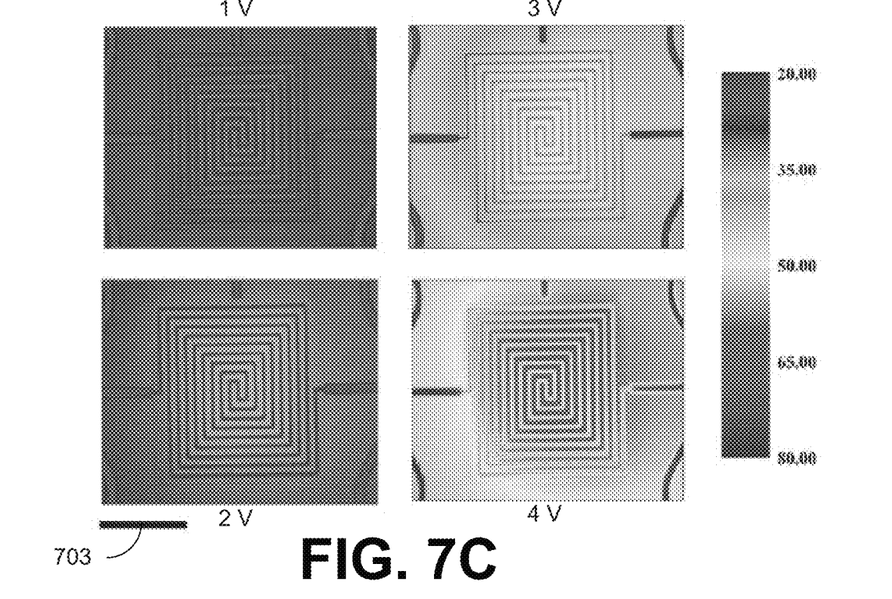

Referring to FIGS. 6B and 7B, shown are plots of the temporal response of the heater temperature for a given applied voltage. The glass substrate was also seen to heat up gradually to a certain temperature for a specific applied voltage. The power was switched on after the indicated "Power On" time. In FIG. 6B, the applied voltage for the thermal patch 100a with $\lambda$=100 μm was varied from about 1 V to about 1.6 V in steps of about 0.1 V (as indicated by the arrow). In FIG. 7B, the applied voltage for the thermal patch 100b with $\lambda$=200 μm was varied from about 2.6 V to about 4 V in steps of about 0.2 V (as indicated by the arrow). FIGS. 6C and 7C are plots of temperature of the thermal patches 100 for various applied voltages for thermal patch designs 100 with =100 μm and $\lambda$=200 μm, respectively. Voltages of 0.5 V (top left), 1.0 V (bottom left), 1.5 V (top right) and 2.0 V (bottom right) were applied in FIG. 6C and 1 V (top left), 2 V (bottom left), 3 V (top right) and 4 V (bottom right) were applied in FIG. 7C. The scale bars 603 and 703 are 2 mm.

The thermal patches 100 were designed such that the widths of the copper lines 112 on the heating pads 103 (50 μm) were half and quarter of the copper lines on the stretchable conductors 109 for $\lambda$=100 μm and $\lambda$=200 μm, respectively. Also, the copper lines 112 on the heating pads 103 were designed so as to maximize their length. Hence, most of the resistance of the thermal patch devices 100 was concentrated across the heating pads 103. This maximized the amount of power dissipated on the heating pad 103, and hence maximized the heating being applied. With this design, the total resistance of the thermal patches 100 was measured to be 8.85 Ohm, including the contact metal resistance. The ratios of the resistance of the heating pad 103 and the stretchable conductors 109 were calculated to be 3.35 and 15.5 for $\lambda$=100 μm and $\lambda$=200 μm, respectively. The high difference in resistance ratios can be mainly attributed to the lower width of copper lines ($\lambda$/4 in case of $\lambda$=200 μm as compared to $\lambda$/2 in case of $\lambda$=100 μm), and because of the larger length of the heating lines (6.84 cm in case of =200 μm as compared to 14.8 cm in case of $\lambda$=100 μm). Hence, for a given current, the ratio of power dissipated on the heating pads to the total power supplied is calculated to be 0.92 and 0.69 for the $\lambda$=200 μm and $\lambda$=100 μm designs, respectively. Thus, in terms of heat dissipation on the heating pads, the design with $\lambda$=200 μm was found to be more efficient.

Figure 8A:
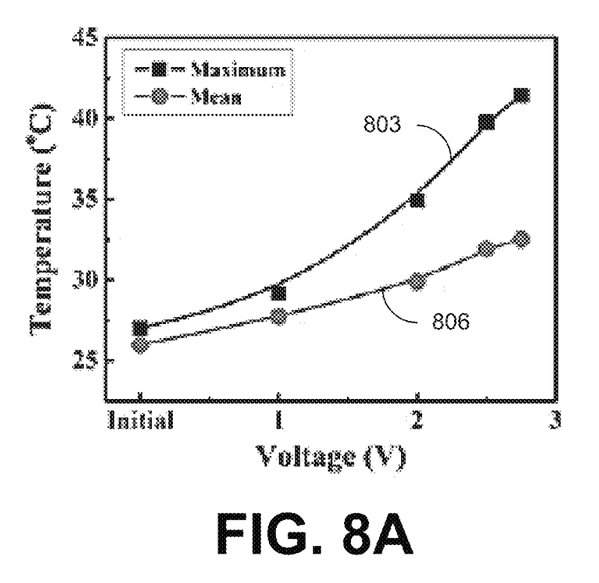
FIGS. 8A-8C are examples of plots of temperature variation plots of temperature of the thermal patches 100 for various applied voltages in accordance with various embodiments of the present disclosure.
Figure 8B:
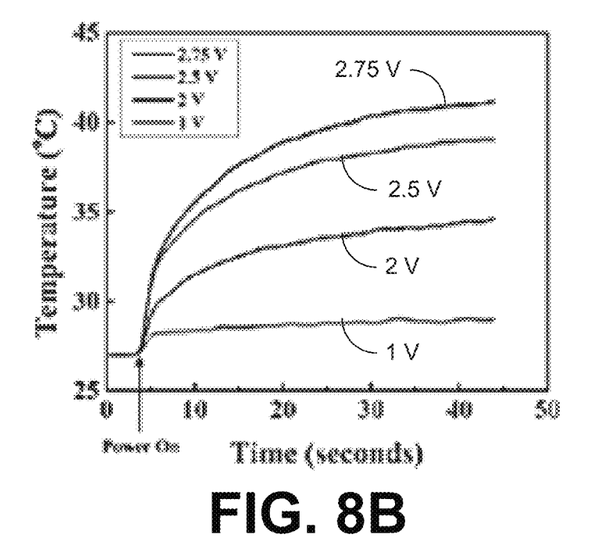

The thermal patch with λ=200 μm was also tested on a consenting, adult human subject (in compliance with Institutional Bioethics Policy). The thermal patch 100b was taped on the hand of the subject using double sided scotch tape. The thermal patch 100b was powered using a constant voltage DC power supply, and the temperatures of the pad and the skin were measured. Referring to FIG. 8A, shown is a plot of the maximum and mean temperatures attained (curves 803 and 806, respectively) versus applied voltage, at 60 seconds after application of the voltage. The mean temperature 806 was calculated for the entire area of the thermal patch 100b, just after switching off the power supply. It was found that the thermal patch 103b effectively heated the human skin up to several degrees over the normal temperature. FIG. 8B plots the temporal response of the skin temperature for given applied voltages of 1 V, 2 V, 2.5V and 2.75 V. The power was switched on after the indicated "Power On" time.

Figure 8C:
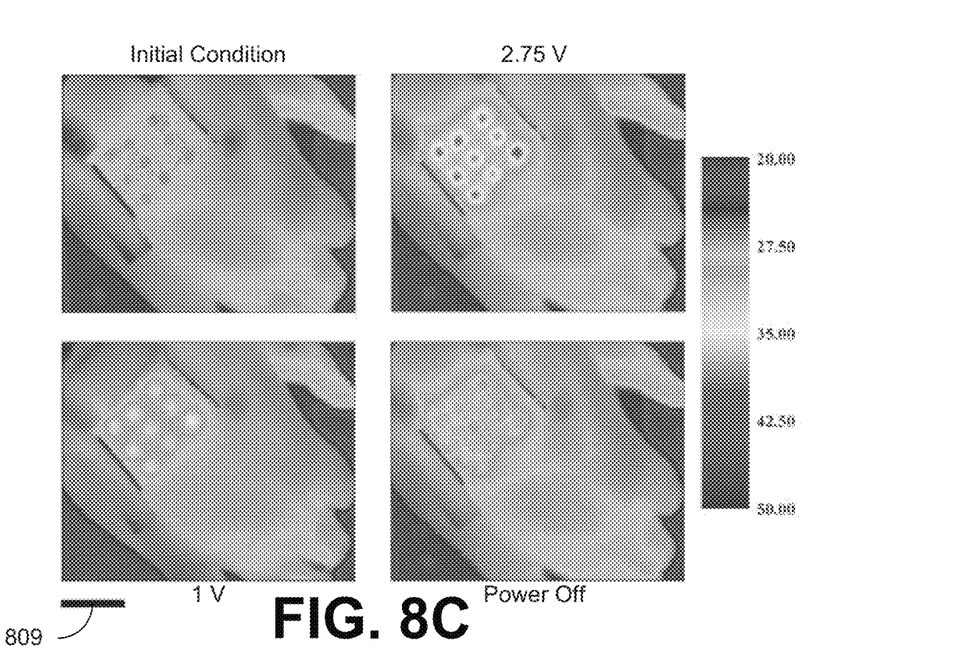

Further, the heating effect was not only under the heating pads 103, but had also extended to the entire region of the thermal patch 100b. This was observed by measuring the mean temperature of the skin just after the power to the thermal patch 100b was switched off. FIG. 8C shows examples of temperature of the skin for various heat application conditions. The initial temperature conditions for the skin and thermal device is show at the top left. The temperature changes caused by applying 1 V after 60 seconds is shown at the bottom left and caused by applying 2.75 V after 60 seconds is shown at the top right. The temperature just after switching the power off, having applied 2.75 V for 60 seconds, is shown at the bottom right. The scale bar 809 is 2 cm. Thus, it was observed that in real application conditions, and under a high strain of 150%, the thermal patch 100b can bring about uniform temperature increment on the human skin.

The stretchable and flexible thermal patches 100 have several applications in the biomedical industry. A thermal patch 100 can be stretched up to 3 times its original size and can be applied to any part of the human body, and may be reused thereafter, for thermotherapy. In many real life applications, a wired constant voltage power supply is not available for use, and can be impractical to carry around for thermotherapy. Hence, a practical thermal patch system can be wireless to be portable and easily usable. Also, as an additional function, the thermal patch 100 should be easily controllable using a readily available device such as, e.g., a smart phone or tablet. To this effect, a thermal patch 100 that is wirelessly controllable using Bluetooth enabled Android-based smart phones was examined. The wireless connectivity was achieved using an open source hardware module (Arduino Uno) along with a Seeedstudio Bluetooth shield. The voltage applied to the thermal patch 100 was controlled using a PWM output from one of the outputs of the Arduino system. The thermal patches 100 can also be used in other applications where heating in a defined area is desired. The flexibility of the thermal patches 100 allows them to be positioned on or around non-uniform surfaces and to be molded to fit the area. For example, a thermal patch 100 may be placed around a pipe to apply heating to correct or avoid freezing of fluid in the pipe. The heating temperature of the thermal patch 100 may be controlled to, e.g., avoid damage to the heated component, control heating variations over time, or maintain a constant temperature.

Figure 9A:
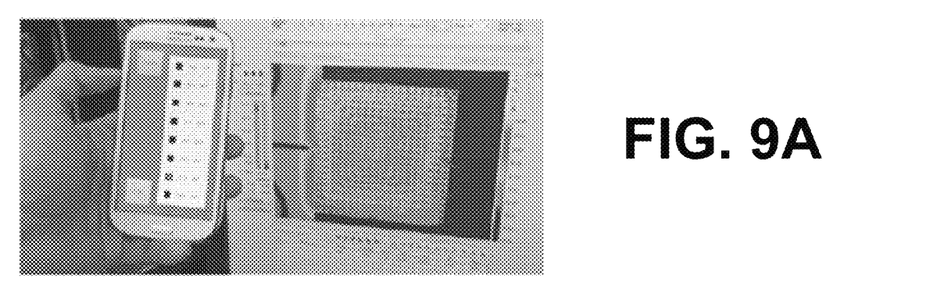
FIGS. 9A and 9B are images of a thermal patch being controlled wirelessly, using a smart phone in accordance with various embodiments of the present disclosure.
Figure 9B:
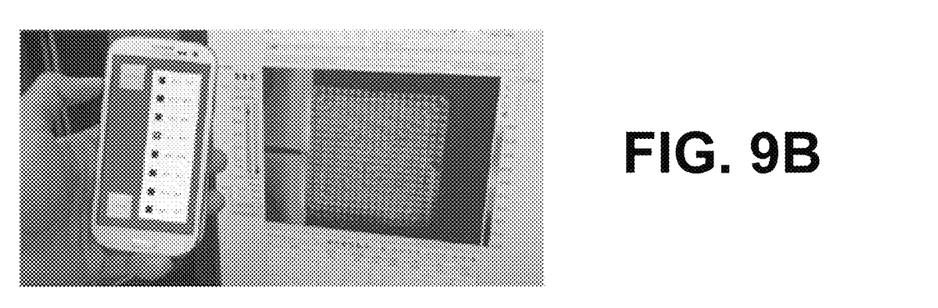

Referring to FIGS. 9A and 9B, shown are images of a thermal patch 100 being controlled wirelessly, using an Android smart phone. These images illustrate the control of temperature of the thermal patch 100 using the smart phone.

The Android-based temperature control system was also tested with human subjects. Using the off-the-shelf Arduino board and its Bluetooth shield in the thermal patch system can make the thermal patch heavy and immobile, which may restrict the full potential of its use as a generic autonomous portable thermotherapy solution. However, using trench-protect-peel-release based transformational silicon electronics to make a flexible microcontroller similar to the one used in the Arduino board can overcome this limitation. Thus, a complete system level solution can be obtained.

Portability of the thermal patch 100 may also be limited by the supply of power from a constant voltage source. In the previous examples, the maximum power drawn by the thermal patch was about 1.5 W. Thus, the thermal patch 100 can be supported by a commercially available coin battery (e.g., a Panasonic CR2477 with capacity of 1000 mAh), for a period of 2 hours, at maximum operating temperature. The battery may also be flexible and stretchable and can be recharged to make the thermal patch 100 reusable. Control of the thermal patch 100 shown in FIGS. 9A and 9B utilizes an open loop control system, wherein the thermal patch 100 and the control software have been calibrated beforehand. In some cases, the control mechanism can lead to inaccuracies in the temperature control of the thermal patch 100. To overcome this problem, the thermal patch 100 can use itself as a temperature sensor.

Since the thermal patch 100 employs copper lines for heating, and the resistance of copper increases with increase in temperature, the resistance of the thermal heating device 100 increases with raising temperature. The resistance can sensed based on the current consumed by the thermal patch 100 in the PWM mode of operation. For example, during testing the temperature response of the resistance of the thermal patch device 100 was tested using a thermal chuck probe station set-up (e.g., Cascade Microsystems M150). The thermal chuck was set at a particular temperature (for 5 minutes at every temperature to achieve steady state), and a small sensing current was applied to the thermal patch 100 to measure the resistance of the thermal patch device 100 without heating it more than the thermal chuck temperature.

Figure 9C:
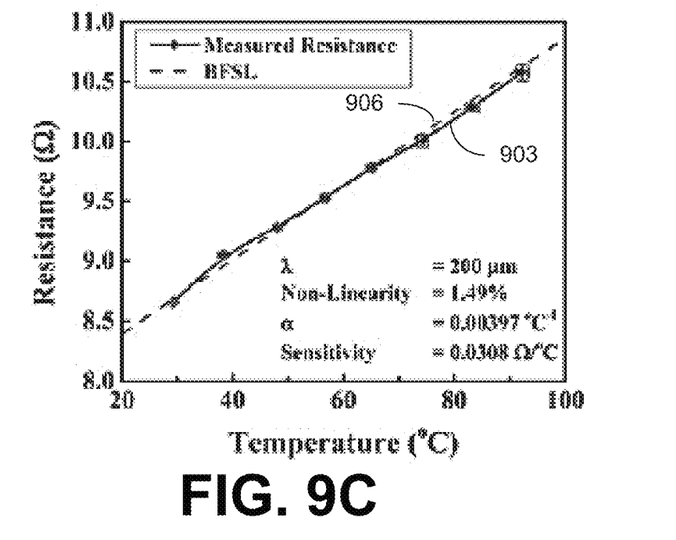
FIG. 9C is an example of a plot of resistance variation of a thermal patch of FIG. 1 with change in temperature in accordance with various embodiments of the present disclosure.

FIG. 9C shows a plot of the variation of resistance of the thermal patch 100 with change in temperature. The error bars indicate the maximum and minimum values of the measured resistance (curve 903) and the chuck temperature (curve 906). As shown in FIG. 9C, the thermal patch 100 can be used as a temperature sensor with a non-linearity of 1.49% in the temperature response of the resistance 903. Further, the sensitivity of the temperature sensor is reported to be 0.0308 Ohm/° C. The temperature co-efficient of resistance (α) for copper was determined to be 0.00397° $C.^{-1}$. Therefore, the current levels in the thermal patch 100 can be used to sense the temperature of the thermal patch 100. This temperature feedback can be used to implement a closed loop control system such that the temperature control of the thermal patch 100 is accurate, which allows the whole system to be adaptable.

Figure 9D:
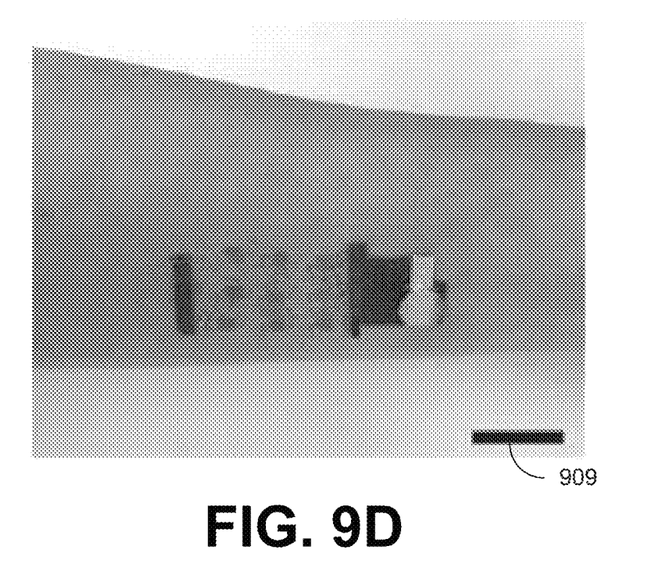
FIG. 9D is an image of an example of a thermal patch of FIG. 1 with flexible controller and a battery in accordance with various embodiments of the present disclosure.

FIG. 9D is an image of an example of a thermal patch design 100 with a flexible silicon microcontroller for wireless temperature control and a coin battery as the power supply. The scale bar 909 is 2 cm. Cost calculations indicate that such an autonomous system can be within about $1-$2, which is a cost effective solution compared to many other status-quo solutions or products. A small flexible silicon piece can be used to house microprocessors and other communication devices, while a coin battery can provide power to the electronics as well as the thermal patch 100 for several hours of operation. Finally, integration of logic processors and memory can add functionality for constantly monitoring a patient, storing the data locally, communicating the in-situ processed data to another computing device or a cloud computing platform, which enabling big data analysis.

The current disclosure describes various examples of thermal patches 100 with wireless control capabilities. To overcome limited stretching capabilities in widely used low-cost metallic thin film copper (Cu), a lithographically patterned mechanical design was used to desorb the deformation strain allowing 800% stretchability while maintaining its high conductivity. A geometrically and spatially tunable, readily usable, affordable thermal patch 100 for thermotherapy was engineered using the flexible spring design. The resulting thermal patch 100 is usable at various locations on human body by providing conformal attachment to irregular skin contours and irregular sizes and shapes of inflamed areas. The thermal contact areas, which can be used as a temperature sensor, allows the patch to adapt to the inflamed area's condition by adjusting the therapy based on the measured temperature of the inflamed area. Wireless interface and battery integration make the system an autonomous, portable and adaptable unit with precise temperature control using smart phones or mobile device.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

What is claimed is:

1. A thermal patch, comprising:
   first and second heating pads; and
   a stretchable metallic electrical conductor interconnecting the first and second heating pads,
   wherein the first heating pad includes a first non-porous polymer pad having plural first through holes made at a given distance from each other, and a first metallic line formed between the plural first through holes, on the first polymer pad, for heating,
   wherein the second heating pad includes a second non-porous polymer pad having plural second through holes made at the given distance from each other, and a second metallic line formed between the plural second through holes, on the second polymer pad, for heating,
   wherein the first polymer pad is separated from the second polymer pad,
   wherein a first end of the stretchable metallic electrical conductor is connected to the first metallic line, and a second end of the stretchable metallic electrical conductor is connected to the second metallic line,
   wherein the stretchable metallic electrical conductor is configured to have a figure "8" configuration to undergo lateral elongation between the first and second heating pads, and
   wherein a width of each of the first and second metallic lines is a fraction of a width of the stretchable metallic electrical conductor so that an amount of power dissipated to the first and second heating pads is maximized.

2. The thermal patch of claim 1, wherein the first and second heating pads and the stretchable metallic electrical conductor are positioned between a plurality of contact pads.

3. The thermal patch of claim 2, wherein each of the first and second heating pads is connected to a corresponding contact pad of the plurality of contact pads by an additional corresponding stretchable metallic electrical conductor.

4. The thermal patch of claim 3, further comprising a battery electrically coupled to at least one of the plurality of contact pads.

5. The thermal patch of claim 1, further comprising a flexible microcontroller.

6. The thermal patch of claim 1, further comprising a wireless transceiver configured to communicate with a mobile computing device.

7. The thermal patch of claim 6, wherein the wireless transceiver is a Bluetooth transceiver.

8. The thermal patch of claim 1, wherein the stretchable metallic electrical conductor has a maximum uniaxial stretchability of 800%.

9. The thermal patch of claim 1, wherein, except for the first and second ends of the stretchable metallic electrical conductor, the stretchable metallic electrical conductor is neither attached to the first and second polymer pads, nor to a substrate.

10. The thermal patch of claim 1, further comprising an array of heating pads that includes the first and second heating pads, and additional stretchable metallic electrical conductors interconnecting corresponding adjacent pairs of heating pads in the array.

11. The thermal patch of claim 1, wherein the width of the first and second metallic lines is half of the width of the stretchable metallic electrical conductor.

12. The thermal patch of claim 1, wherein the width of the first and second metallic lines is one quarter of the width of the stretchable metallic electrical conductor.

13. The thermal patch of claim 1, wherein the stretchable metallic electrical conductor has an overall lateral length equal to ten times the width of the stretchable metallic electrical conductor.

14. The thermal patch of claim 10, wherein the array of heating pads is positioned between a plurality of contact pads and at least some heating pads of the array of heating pads are connected to at least one contact pad of the plurality of contact pads by corresponding stretchable metallic electrical conductors configured to undergo lateral elongation between the heating pad and the contact pad.

15. The thermal patch of claim 14, wherein each of the corresponding stretchable metallic electrical conductors has a lateral spring configuration.

16. A thermal patch, comprising:
first and second heating pads, each of the first and second heating pads having corresponding plural through holes, and the first and second heating pads having first and second metallic lines formed between the plural through holes, respectively; and
a stretchable metallic electrical conductor interconnecting the first metallic line of the first heating pad to the second metallic line of the second heating pad,
wherein the first heating pad is separated from the second heating pad, and
wherein a width of each of the first and second metallic lines is a fraction of a width of the stretchable metallic electrical conductor so that an amount of power dissipated to the first and second heating pads is maximized.

17. The thermal patch of claim 16, wherein the stretchable metallic electrical conductor is configured to have a figure "8" configuration to undergo lateral elongation between the first and second heating pads.

18. The thermal patch of claim 16, wherein the first and second heating pads and the stretchable metallic electrical conductor are positioned between a plurality of contact pads, and the thermal patch further comprises:
a battery electrically coupled to at least one of the plurality of contact pads;
a flexible microcontroller; and
a wireless transceiver configured to communicate with a mobile computing device.

19. The thermal patch of claim 18, wherein the wireless transceiver is a Bluetooth transceiver.

20. The thermal patch of claim 16, wherein the stretchable metallic electrical conductor has an overall lateral length equal to ten times the width of the stretchable metallic electrical conductor.

* * * * *